(12) United States Patent
Buettelmann et al.

(10) Patent No.: US 8,569,306 B2
(45) Date of Patent: Oct. 29, 2013

(54) JNK MODULATORS

(75) Inventors: Bernd Buettelmann, Schopfheim (DE); Bindu Goyal, Fremont, CA (US); Wylie Solang Palmer, Morristown, NJ (US)

(73) Assignee: Hoffmann-La Roche, Inc., Nutley, NJ (US)

( * ) Notice: Subject to any disclaimer, the term of this patent is extended or adjusted under 35 U.S.C. 154(b) by 19 days.

(21) Appl. No.: 13/202,779

(22) PCT Filed: Feb. 19, 2010

(86) PCT No.: PCT/EP2010/052084
§ 371 (c)(1),
(2), (4) Date: Aug. 23, 2011

(87) PCT Pub. No.: WO2010/097335
PCT Pub. Date: Sep. 2, 2010

(65) Prior Publication Data
US 2011/0306618 A1    Dec. 15, 2011

Related U.S. Application Data

(60) Provisional application No. 61/154,926, filed on Feb. 24, 2009.

(51) Int. Cl.
A61K 31/497 (2006.01)
A61K 31/505 (2006.01)
C07D 403/00 (2006.01)
C07D 401/00 (2006.01)

(52) U.S. Cl.
USPC ...... 514/252.18; 514/275; 435/184; 544/295; 544/331

(58) Field of Classification Search
USPC .............. 514/252.18, 275; 435/184; 544/295, 544/331
See application file for complete search history.

(56) References Cited

U.S. PATENT DOCUMENTS

| 2008/0103142 A1 | 5/2008 | Goldstein et al. |
| 2008/0146565 A1 | 6/2008 | Dunn et al. |

FOREIGN PATENT DOCUMENTS

| WO | 2006/038001 | 4/2006 |
| WO | 2008/068171 | 6/2008 |

OTHER PUBLICATIONS (International Search Report for PCT/EP2010/052084 Apr. 6, 2010).
Buckley, G.M. et al., Bioorganic & Medicinal Chemistry Letters 18:3291-3295 ( 2008).
Alam, M. et al., Bioorganic & Medicinal Chemistry Letters 17:3463-3467 ( 2007).
Francescato et al., Nephrol. Dial Transplant 22:2138-2148 ( 2007).
Bradley et al., J. Allergy Clin. Immunol. 88:661-674 ( 1991).
Bozyczko-Coyne et al., Current Drug Targets—CNS & Neurological Disorders 1:31-49 ( 2002).
Gaillard et al., J. Med. Chem. 48:4596-4607 ( 2005).
Antonyak et al., Oncogene 21:5038-5046 ( 2002).
Saporito et al., Journal of Neurochemistry 75:1200-1208 ( 2000).
Manning et al., Nat. Rev. Drug Discov. 2:554-565 (Jul. 2003).
Han, Z et al., Journal of Clinical Investigation 108:73-81 ( 2001).
Derijard et al., Cell 76:1025-1037 (Mar. 1994).
Ip et al., Current Opinion in Cell Biology 10:205-219 ( 1998).
Wang, Y. et al., Life Sciences 80:2067-2075 ( 2007).
Kaneto et al., Expert Opin. Ther. Targets 9(3):581-592 ( 2005).
Lee, Y.H. et al., The Journal of Biological Chemistry 278(5):2896-2902 (Jan. 2003).
Kaneto et al., Nature Medicine 10(10):1128-1132 (Oct. 2004).
Flanc et al., Kidney International 72:698-708 ( 2007).
Hirosumi et al., Nature 420:333-336 (Nov. 2002).
Yang, D.D. et al., Nature 389:865-870 (Oct. 1997).
Xia et al., Proc. Natl. Acad. Sci. USA 98(18):10433-10438 (Aug. 2001).
Cripe et al., Leukemia 16:799-812 ( 2002).
Bennett et al., Current Opinion in Pharmacology 3:420-425 ( 2003).
Nath et al., European Journal of Pharmacology 506:273-283 ( 2005).
Pei et al., Journal of Alzheimer's Disease 3:41-48 ( 2001).
Jaeschke et al., Proc. Natl. Acad. Sci. USA 102(19):6931-6935 (May 2005).
Han, Z. et al., Arthritis & Rheumatism 46(3):818-823 (Mar. 2002).
Blease et al., Expert Opin. Emerging Drugs 8(1):71-81 ( 2003).
Kujime et al., J. Immunol. 164:3222-3228 ( 2000).
Hess et al., Nature Genetics 32:201-205 (Sep. 2002).

(Continued)

*Primary Examiner* — Jennifer M Kim

(57) ABSTRACT

Compounds of formula (I) modulate JNK wherein $X^1$ and $X^2$ are each simultaneously N or CH; $X^3$ is CH—$R^2$ Or N—$SO_2R$, where R is lower alkyl; $R^1$ is aryl or heteroaryl, substituted with 0-3 lower alkyl radicals; $R^2$ is (II), where $R^3$ is H, lower acyl, or an amino acid, or a pharmaceutically acceptable salt thereof.

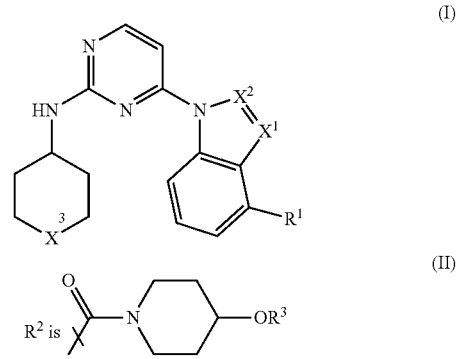

14 Claims, No Drawings

(56) References Cited

OTHER PUBLICATIONS

Yasuda et al., Molecular and Cellular Biology 19(10):7245-7254 (Oct. 1999).
Grande et al., Current Medicinal Chemistry 15:2054-2070 (2008).
Sundarrajan et al., Arthritis & Rheumatism 48(9):2450-2460 (2003).
Nakatani et al., The Journal of Biological Chemistry 279(44):45803-45809 (Oct. 2004).
Bousquet et al., Am. J. Respir. Crit. Care Med. 161:1720-1745 (2000).
Eynott et al., British Journal of Pharmacology 140:1373-1380 (2003).
Schett et al., Arthritis & Rheumatism 43(11):2501-2512 (Nov. 2000).

JNK MODULATORS

This application is the National Stage of International Application No. PCT/EP2010/052084, filed Feb. 19, 2010, which claims the benefit of U.S. provisional application 61/154,926, filed Feb. 24, 2009, which is hereby incorporated by reference in its entirety.

The present invention relates to a method for modulating c-Jun N-terminal kinases (JNK), and a method for treating a subject afflicted with a disease or condition that can be alleviated by modulating JNKs with heterocyclic compounds. The invention further relates to novel heterocyclic compounds and pharmaceutical compositions comprising said compound.

The c-Jun N-terminal kinases (JNKs) are members of mitogen-activated protein kinase family along with p38 and extracellular signal-regulated kinases (ERKs). Three distinct genes (jnk1, jnk2 and jnk3) encoding 10 splice variants have been identified (Y. T. Ip and R. J. Davis, Curr. Opin. Cell Biol. (1998) 10:205-19). JNK1 and JNK2 are expressed in a wide variety of tissues, whereas JNK3 is mainly expressed in neurons, and to a lesser extent in heart and testes (D. D. Yang et al., Nature (1997) 389:865-70). Members of JNK family are activated by pro-inflammatory cytokines such as tumor necrosis factor α (TNF-α) and interleukin-1β (IL-1β), as well as environmental stresses. The activation of JNKs is mediated by its upstream kinases, MKK4 and MKK7, via dual phosphorylation of Thr-183 and Tyr-185 (B. Derijard et al., Cell (1994) 76:1025-37). It has been shown that MKK4 and MMK7 can be activated by the diverse upstream kinases, including MEKK1 and MEKK4, depending upon the external stimuli and cellular context (D. Boyle et al., Arthritis Rheum (2003) 48:2450-24). The specificity of JNK signaling is achieved by forming a JNK-specific signaling complex containing multiple components of the kinase cascade using scaffold proteins called JNK-interacting proteins (J. Yasuda et al., Mol. Cell. Biol. (1999) 19:7245-54). JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2 (A. M. Manning and R. J. Davis, Nat. Rev. Drug Discov. (2003) 2:554-65). Over-activation of JNK is believed to be an important mechanism in autoimmune, inflammatory, metabolic, neurological diseases as well as cancer and pain.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients (G. Schett et al., Arthritis Rheum (2000) 43:2501-12) and rodent arthritic joints from animal models of arthritis (Z. Han et al., J. Clin. Invest. (2001) 108:73-81). In addition, inhibition of JNK activation by selective JNK inhibitors blocked proinflammatory cytokines and MMP production in human synoviocytes, macrophages and lymphocytes (Z. Han et al., (2001) supra) Importantly, administration of the selective JNK inhibitors in rats with adjuvant arthritis (Z. Han et al., (2001) supra) or in mice with collagen-induced arthritis (P. Gaillard et al., J Med. Chem. (2005) 14:4596-607) effectively protected joints from destruction and significantly reduced paw swelling by inhibiting cytokine and collagenase expression. Furthermore, JNK2 deficient mice were partially protected from joint destruction, but showed little effect on paw swelling and inflammation in the passive collagen-induced arthritis model. These studies indicate that JNK2 is functionally redundant with JNK1 in regard to their roles in matrix degradation, inflammation and paw swelling. Therefore, combined inhibition of both JNK1 and JNK2 activities is required for effective therapy for RA (Z. Han et al., Arthritis Rheum. (2002) 46:818-23).

Asthma is a chronic inflammatory disease of airways, characterized by the presence of a cellular inflammatory process and by bronchial hyper-responsiveness associated with structural changes of the airways (B. Bradley et al., J. Allergy Clin. Immunol. (1991) 88:661-74). This disorder has been shown to be driven by many cell types in the airways, including T lymphocytes, eosinophils, mast cells, neutrophils and epithelial cells (J. Bousquet et al., Am. J. Respir. Crit. Care Med. (2000) 161:1720-45). JNKs have emerged as promising therapeutic targets for asthma based upon the recent proof-of-concept studies in the cellular and animal models of asthma using selective JNK inhibitors (K. Blease et al., Expert Opin. Emerg. Drugs (2003) 8:71-81). It was shown that JNK inhibitors significantly blocked RANTES production in activated human airway smooth cells (K. Kujime et al., J. Immunol. (2000) 164:3222-28). More importantly, the JNK inhibitors showed good efficacy in chronic rat and mouse models for their abilities to reduce cellular infiltration, inflammation, hyper-responsiveness, smooth muscle proliferation, and IgE production (P. Nath et al., Eur. J. Pharmacol. (2005) 506:273-83; P. Eynott et al., Br. J. Pharmacol. (2003) 140:1373-80). These observations suggest important roles of JNKs in the allergic inflammation, airway remodeling process associated with hyperresponsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions (J. Hirosumi et al., Nature (2002) 420: 333-36; H. Kaneto, Expert. Opin. Ther. Targets (2005) 9:581-92). Activation of the JNK pathway by pro-inflammatory cytokines and oxidative stresses negatively regulates insulin signaling via phosphorylation of insulin receptor substrate-1 (IRS-1) at Ser$^{307}$, therefore contributes to insulin resistance and glucose tolerance (J. Hirosumi et al., Nature (2002) supra; Y. Lee et al., J. Biol. Chem. (2003) 278:2896-902; Y. Nakatani et al., J. Biol. Chem. (2004) 279:45803-09). Compelling genetic evidence came from elegant animal model studies using jnk$^{-/-}$ mice crossed with either genetic (ob/ob) obese mice or dietary obese mice. Loss of JNK1(JNK1$^{-/-}$), but not JNK2 functions (jnk2$^{-/-}$), protected obese mice from body gains, increased steady-state levels of blood glucose, and decreased plasma insulin levels (J. Hirosumi et al., Nature (2002) supra). Furthermore, the beneficial effects were observed in a genetic diabetic model (db/db mice) by administration of either a small molecule JNK inhibitor, CC105 (B. Bennett et al., Curr. Opin. Pharmacol. (2003) 3:420-25) or a JNK inhibitory peptide PIP) derived from the JNK binding domain of the JNK-interacting protein-1 (JIP-1) (H. Kaneto et al., Nat. Med. (2004) 10:1128-32), including significant lower blood glucose and higher plasma insulin levels. More interestingly, another recent report (A. Jaeschke et al., Proc. Natl. Acad. Sci. USA. (2005) 102:6931-35)

revealed that JNK2 plays an important role in type 1 diabetes caused by autoimmune destruction of insulin-producing β cells. Non-obese diabetic mice deficient in JNK2 expression showed reduced destructive insulitis and less disease progression to diabetes, probably due to biased polarization toward the Th2 phenotype. Taken together, these studies demonstrated the utility of JNK inhibitors in the treatment of obesity/type 2 diabetes.

Neurodegenerative diseases, such as Alzheimer's (AD), Parkinson's (PD) and stroke are characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli (D. Bozyczko-Coyne et al., *Curr. Drug Targets CNS Neurol. Disord.* (2002) 1:31-49). Over-activation of JNK was observed in human brains from AD patients (J. Pei et al., *J. Alzheimers Dis.* (2001) 3:41-48) or rodent brain sections derived from animal models of neurodegenerative diseases (M. Saporito et al., *J. Neurochem.* (2000) 75:1200-08). For example, increased phospho-JNKs were detected in the postmortem brains from the AD patients. Administration of JNK inhibitory peptide (JIP-1 peptide) in the rodent model of AD induced by β-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra (X. Xia et al., *Proc. Natl. Acad. Sci. USA.* (2001) 98:10433-38). In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death (D. D. Yang et al., *Nature* (1997) 389:865-70). These data suggest JNK3 was mainly responsible for glutamate excitotoxicity, an important component in ischemic conditions. Taken together, the data suggests that JNKs are an attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts (M. Antonyak et al., *Oncogene* (2002) 21:5038-46; P. Hess et al., *Nat. Genet.* (2002) 32:201-05). In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML patients has been causally linked to the sustained JNK activity present in these AML samples (L. Cripe et al., *Leukemia* (2002) 16:799-812). Activation of JNK in leukemic cells resulted in induced expression of efflux pumps such as mdr1 and MRP1 responsible for multidrug resistance. Also, genes with a survival benefit in response to oxidative stress including glutathione-5-transferase π and γ-glutamyl cysteine synthase were also upregulated by the activated JNK pathway.

Acute Renal Failure (ARF) is an abrupt and sustained decrease in renal function associated with renal ischemia or nephrotoxic insult. ARF can be induced by multiple causes (including trauma and sepsis), and is the cause of significant morbidity and mortality. In vitro evidence suggests that JNK activation plays a critical role in alterations in kidney mesangial cell function associated with glomerular disease, and activation of kidney JNK in vivo has been reported in both ischemic and nephrotoxic animal models of ARF (Grande and Lopez-Novoa, *Curr. Med. Chem.* (2008) 14:2054-70). JNK inhibitors have been shown to ameliorate kidney damage in renal ischemia/reperfusion (Wang et al., *Life Sci.* (2007) 80:2067-75) and nephrotoxic (Cisplatin or anti-glomerular basement membrane induced) models (Francescato et al., *Nephrol. Dial. Transplant.* (2007) 22:2138-48; Flanc et al., *Kidney Intl.* (2007) 72:698-708). JNK therefore presents as a novel therapeutic target for the treatment and/or prevention of ARF.

Accordingly, JNK modulators are useful in treating a variety of diseases and/or conditions.

One aspect of the invention provides a compound of formula I:

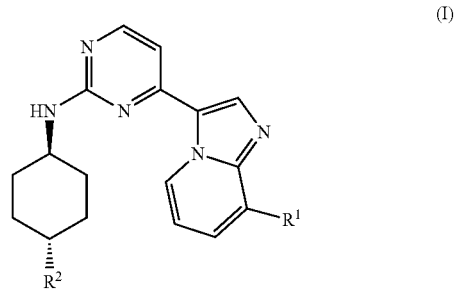

wherein $R^1$ is H, —OH, —OR, or hydroxy-lower alkyl, where R is lower alkyl, benzyl, aryl-lower alkyl, or methylsulfonyl-lower alkyl; $R^2$ is —OH, —NH$_2$, —SO$_2$R$^4$, —NHSO$_2$R$^4$, —CO$_2$R$^5$, or

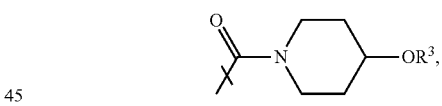

where $R^3$ is H, lower acyl, or an amino acid; $R^4$ is lower alkyl, —NH$_2$, lower alkyl-amino, or di(lower alkyl)amino; $R^5$ is H or lower alkyl; or a pharmaceutically acceptable salt thereof.

The invention also provides pharmaceutical compositions, methods of using, and methods of preparing the aforementioned compounds.

Compounds and compositions of the invention are useful in the treatment and/or prevention of a c-Jun N-terminal kinase mediated disorder, such as autoimmune disorders, inflammatory disorders, metabolic disorders, neurological diseases, pain, and cancer. In some embodiments, compounds and compositions of the invention are useful in treating and/or preventing rheumatoid arthritis, asthma, type II diabetes, acute renal failure, Alzheimer's disease, Parkinson's disease and/or stroke.

DEFINITIONS

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" refers to an alkyl moiety having at least one branch, for example, isopropyl, isobutyl, tert-butyl, and the like. Similarly, "lower alkoxy" refers to a moiety of the form —OR, and "acyl" refers to a moiety of the form —C(O)R, where R is lower alkyl.

"Alkylene" means a linear saturated divalent hydrocarbon moiety of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylene dioxy" means a divalent moiety of the formula —O—R—O—, where R is alkylene as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Heteroaryl" means a monocyclic moiety of 5 to 7 ring atoms having one, two, or three ring heteroatoms selected from N, O, or S, the remaining ring atoms being C. The heteroaryl ring may be optionally substituted as defined herein. Examples of heteroaryl moieties include, without limitation, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, pyridazinyl, and the like, including partially hydrogenated derivatives thereof.

The terms "halo," "halogen," and "halide" are used interchangeably herein and refer to a substituent fluoro, chloro, bromo, or iodo. The term "oxo" refers to a double-bonded oxygen, i.e., =O. The term "ketal" as used herein refers to a ketone derivative, wherein two alkoxy groups are bound to the same carbon atom, or both ends of a group of the formula —O-(lower alkyl)-O— are bound to a single carbon atom.

The term "amino acid" as used herein refers to an organic moiety having both an amine group and a carboxylic acid group. Exemplary amino acids include alanine, β-alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine.

"Optionally substituted" means that the referenced radical can be substituted independently with one or more substituents, preferably one to four, and more preferably, one to three substituents as set forth. For example, "cycloalkyl optionally substituted with OH" would include all cycloalkyl radicals within the definition thereof, unsubstituted or substituted with one or more hydroxy groups. Exemplary groups meeting that description include, without limitation, cyclobutyl, cyclohexyl, cyclopentyl, cyclopropyl, 2-hydroxycyclobutyl, hydroxycyclopropyl, 3,4-dihydroxycyclohexyl, 3-hydroxycyclopentyl, and the like.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzene-sulfonyloxy, tosyloxy, and thienyloxy, dihalophosphinoyloxy, optionally substituted benzyloxy, isopropyloxy, acyloxy, and the like.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate, sodium hydroxide, and the like.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

"Protective group" or "protecting group" indicate a chemical group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The term "anaerobic atmosphere" as used herein refers to an atmosphere that generally excludes oxygen. A reaction conducted under an anaerobic atmosphere may be conducted by, for example, bubbling nitrogen or argon (or another inert gas) through the reaction mixture, and preferably also degassing the reactants. The term "elevated pH" refers to a reaction mixture having a moderately strong base present, such as, for example, $Na_2CO_3$, whether the reaction mixture is entirely aqueous or not. The term "elevated temperature" as used herein refers to reaction temperatures in excess of 70° C., typically in excess of 105° C.

Compounds of Formula I are useful for, without limitation, the treatment of inflammation and/or pain in a subject. Compounds of the invention can be used to treat pain and inflammation caused by arthritis, including without limitation, rheumatoid arthritis, spondyloarthropathies, gouty arthritis, osteoarthritis, systemic lupus erythematosus and juvenile arthritis, osteoarthritis, gouty arthritis and other arthritic conditions. Such compounds are also useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of inflammation caused by viral and bacterial infections, including sepsis, septic shock, gram negative sepsis, malaria, meningitis, cachexia secondary to infection or malignancy, pneumonia, and herpes virus.

"Pain" means the more or less localized sensation of discomfort, distress, or agony, resulting from the stimulation of specialized nerve endings. There are many types of pain, including, without limitation, lightning pains, phantom pains, shooting pains, acute pain, inflammatory pain, neuropathic pain, complex regional pain, neuralgia, neuropathy, and the like (Dorland's Illustrated Medical Dictionary, 28th Edition, W. B. Saunders Company, Philadelphia, Pa.). The goal of treatment of pain is to reduce the degree of severity of pain perceived by a treatment subject. "Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom.

Whenever a chiral carbon is present in a chemical structure, it is intended that all stereoisomers associated with that chiral carbon are encompassed by the structure.

All patents and publications identified herein are incorporated herein by reference in their entirety.

General Method

One aspect of the invention provides a compound of formula I:

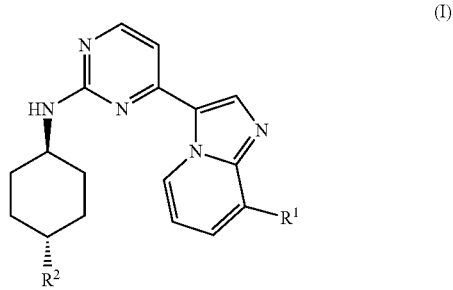

(I)

wherein $R^1$ is H, —OH, —OR, or hydroxy-lower alkyl, where R is lower alkyl, benzyl, aryl-lower alkyl, or methylsulfonyl-lower alkyl;

$R^2$ is —OH, —NH$_2$, —CH$_2$SO$_2$R$^4$, —SO$_2$R$^4$, —NHSO$_2$R$^4$, —CO$_2$R$^5$, or

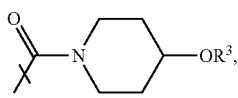

where R³ is H, lower acyl, or an amino acid; R⁴ is lower alkyl, —NH₂, lower alkyl-amino, or di(lower alkyl)amino; R⁵ is H or lower alkyl; or a pharmaceutically acceptable salt thereof.

In some embodiments, the invention provides a compound of formula I:

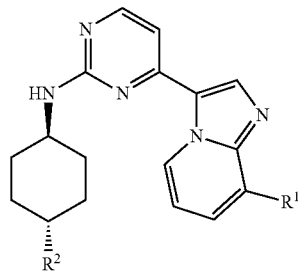

(I)

wherein R¹ is H, —OH, —OR, or hydroxy-lower alkyl, where R is lower alkyl, benzyl, aryl-lower alkyl, or methylsulfonyl-lower alkyl; R² is —OH, —NH₂, —SO₂R⁴, —NHSO₂R⁴, —CO₂R⁵, or

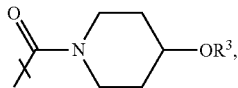

where R³ is H, lower acyl, or an amino acid; R⁴ is lower alkyl, —NH₂, lower alkyl-amino, or di(lower alkyl)amino; R⁵ is H or lower alkyl; or a pharmaceutically acceptable salt thereof.

In some embodiments, R² is —NHSO₂CH₃. In some of these embodiments, R¹ is H, benzyloxy, or 2-hydroxyprop-2-yl.

In some embodiments, R² is 4-hydroxy-piperidin-1-yl-carbonyl. In some of these embodiments, R¹ is H, 3-methane-sulfonylpropoxy, benzyloxy, or 2-hydroxyprop-2-yl.

In some embodiments, R² is —NHSO₂N(CH₃)₂. In some of these embodiments, R¹ is benzyloxy, or 2-hydroxyprop-2-yl.

In some embodiments, R² is —OH. In some of these embodiments, R¹ is H, benzyloxy, or 2-hydroxyprop-2-yl.

In some embodiments, R² is CO₂R⁵. In some of these embodiments, R⁵ is lower alkyl. In some of these embodiments, R⁵ is ethyl. In some of these embodiments, R¹ is H or benzyloxy.

Another aspect of the invention is a method for treating inflammation, comprising administering an effective amount of a compound of the invention to a subject in need thereof.

Another aspect of the invention is a pharmaceutical composition, comprising a compound of the invention and a pharmaceutically acceptable excipient.

It should be appreciated that combinations of the different groups described herein may form other embodiments. In this manner, a variety of different compounds are embodied within the present invention.

Representative compounds of the invention are shown in Table 1 below.

TABLE 1

| Representative compounds of Formula I. | | |
|---|---|---|
| Structure | Name | Compound No. |
| | 2-{3-[2-(4-methanesulfonyl-methyl-cyclohexyl-amino)-pyrimidin-4-yl]-imidazo[1,2-a]pyridine-8-yl}-propan-2-ol<br>Mp = 223-224° C. | 1 |
| | (4-{4-[8-(1-hydroxy-1-methyl-ethyl)-imidazo-[1,2-a]pyridin-3-yl]-pyrimidin-2-ylamino}-cyclohexyl)-(4-hydroxy-piperidin-1-yl)-methanone<br>Mp = 188-190° C. | 2 |

TABLE 1-continued

Representative compounds of Formula I.

| Structure | Name | Compound No. |
|---|---|---|
| | N-(4-{4-[8-(1-hydroxy-1-methyl-ethyl)-imidazo[1,2-a]pyridine-3-yl]-pyrimidin-2-yl-amino}-cyclohexyl)-methanesulfonamide<br>Mp = 249-250° C. | 3 |
| | N-(4-{4-[8-(1-hydroxy-1-methyl-ethyl)-imidazo[1,2-a]pyridine-3-yl]-pyrimidin-2-yl-amino}-cyclohexyl)-(N,N-dimethylamino)-sulfonamide<br>Mp = >300° C. | 4 |
| | (4-hydroxy-piperidin-1-yl)-(4-{4-[8-(3-methane-sulfonyl-propoxy)-imidazo[1,2-a]pyridin-3-yl]-pyrimidin-2-yl-amino}-cyclohexyl)-methanone<br>Mp = 258-259° C. | 5 |
| | {4-[4-(8-benzyloxy-imidazo[1,2-a]pyridin-3-yl)-pyrimidin-2-yl-amino]-cyclohexyl}-(4-hydroxy-piperidin-1-yl)-methanone<br>Mp = 210-212° C. | 6 |

TABLE 1-continued

Representative compounds of Formula I.

| Structure | Name | Compound No. |
|---|---|---|
|  | N-{4-[4-(8-benzyloxy-imidazo[1,2-a]pyridin-3-yl)-pyrimidin-2-yl-amino]-cyclohexyl}-methanesulfonamide<br>Mp = 236.9-241.0° C. | 7 |
|  | 4-[4-(8-benzyloxy-imidazo[1,2-a]pyridin-3-yl)-pyrimidin-2-yl-amino]-cyclohexane-carboxylic acid ethyl ester<br>Mp = 147-149° C. | 8 |
|  | 4-[4-(8-benzyloxy-imidazo[1,2-a]pyridin-3-yl)-pyrimidin-2-yl-amino]-cyclohexanol<br>Mp = 236-238° C. | 9 |
|  | N-[4-(4-imidazo[1,2-a]-pyridin-3-yl-pyrimidin-2-ylamino)-cyclohexyl]-methanesulfonamide<br>Mp = 259-261° C. | 10 |
|  | 4-(4-imidazo[1,2-a]-pyridin-3-yl-pyrimidin-2-ylamino)-cyclohexanol<br>Mp = 255-257° C. | 11 |

Synthesis

Compounds of the present invention can be made by a variety of methods depicted in the illustrative examples shown in the Examples section below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplements; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained herein.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reaction described herein preferably are conducted under inert atmosphere, at atmospheric pressure, at a reaction temperature range of from about −78° C. to about 230° C., and most preferably and conveniently at room (or ambient) temperature, e.g., about 20° C.

In the following schemes, if not differently specified, $R^1$, $R^2$, and the like are as defined above.

SCHEME I:

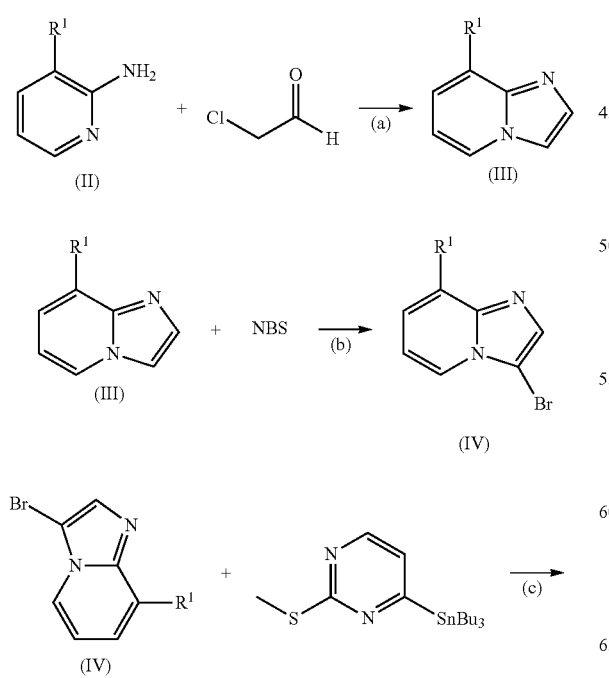

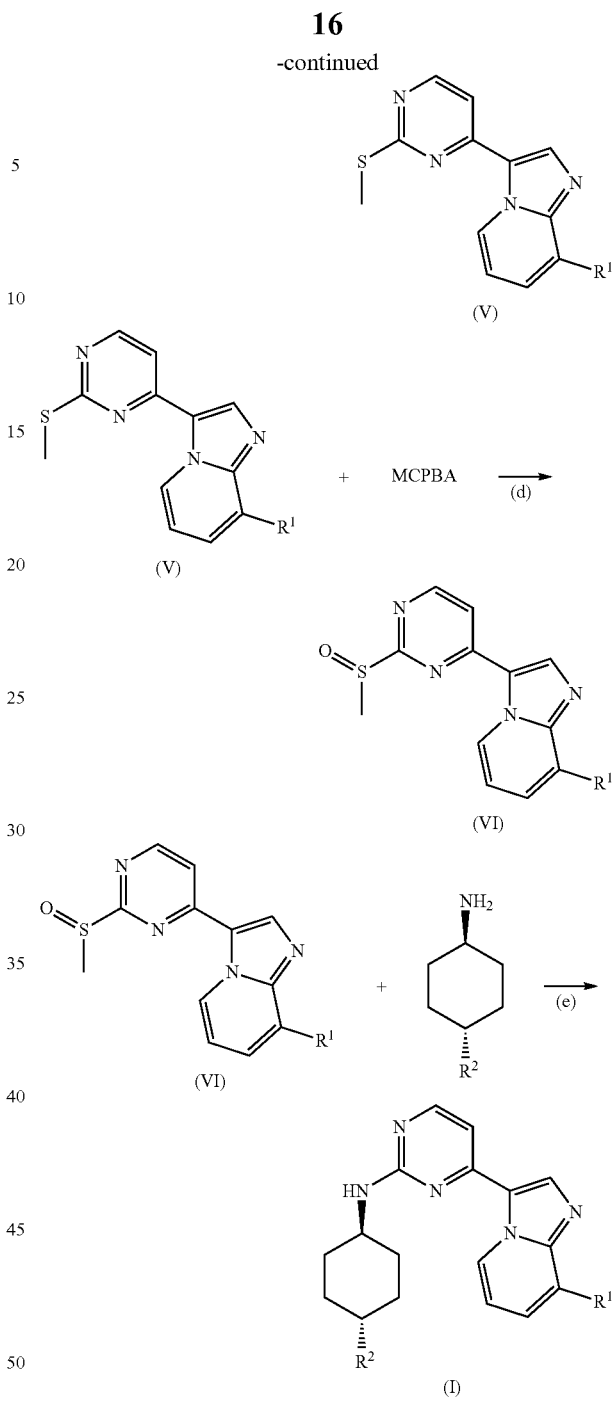

Step (a): A substituted pyridine (II) is condensed with a halo-acetaldehyde using a moderately strong base such as $NaHCO_3$ in an appropriate solvent such as EtOH, heating until the reaction is complete to form imidazole[1,2-a]pyridine intermediate III.

Step (b): Intermediate III is halogenated by standard means, such as by treating the intermediate with NBS in an appropriate solvent, for example DCM at RT, to form Intermediate IV.

Step (c): Intermediate IV is coupled to the methylthiopyrimidine derivative to provide intermediate V, for example using $Pd_2(dba)_3$, Pt—$Bu_3$-$HBF_4$, and CsF in dioxane, heated overnight.

Step (d): The sulfanyl pyrimidine of Intermediate (V) is oxidized to sulfinyl, for example using MCPBA in DCM, to provide Intermediate (VI).

Step (e): The methylsulfinyl radical of Intermediate (VI) is then replaced with 4-amino-cyclohexane derivative by heating in an appropriate solvent, such as NMP in the presence of a moderately strong base, such as tri-ethylamine, to provide the compound of the invention. The $R^2$ substituent may then be further modified, for example without limitation, by esterification, amidation, and the like, to provide other compounds of the invention.

SCHEME II:

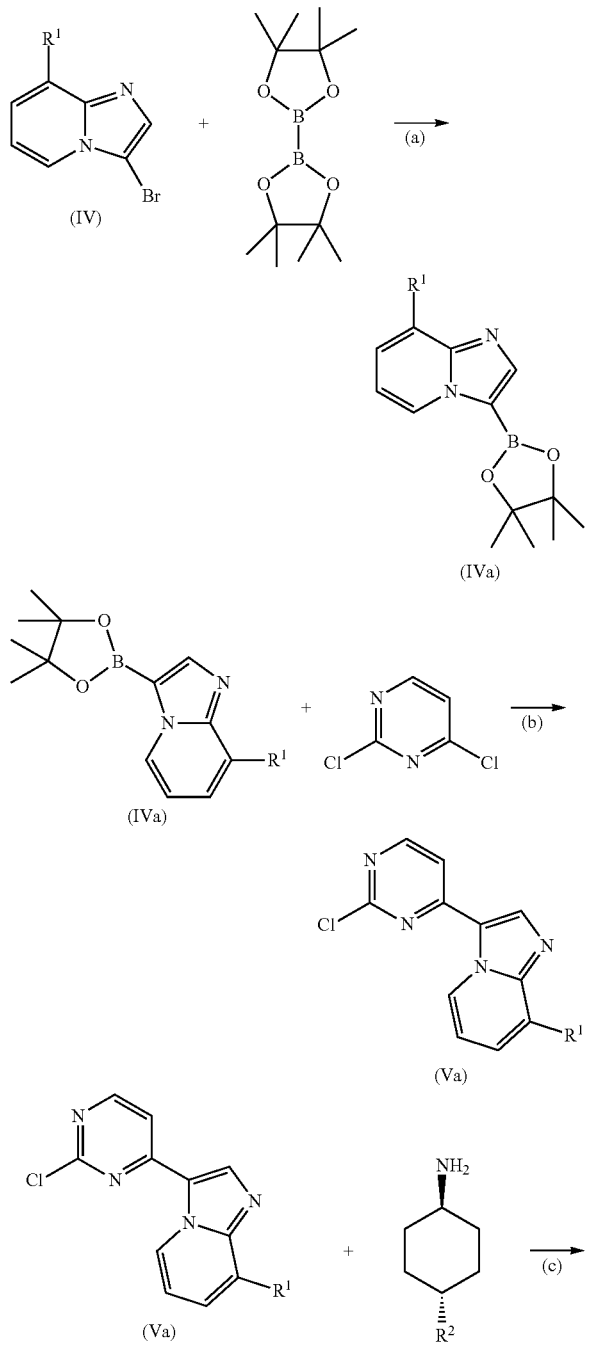

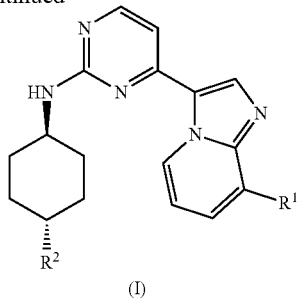

(I)

Step (a): The imidazole[1,2-a]pyridine intermediate IV is treated with a boronic acid ester derivative such as di(tetramethyl-[1,3,2]dioxoborlanyl), using $Pd_2(dba)_3$, $P(cyc)_3$, and KOAc in dioxane to provide Intermediate IVa.

Step (b): Intermediate IVa is treated with dichloropyrimidine, using $PdC(PPh_3)_4$, $Na_2CO_3$, MeCN, and water to provide Intermediate Va.

Step (c): The halo radical of Intermediate (IVa) is then replaced with the substituted cyclohexylamine, for example by heating in NMP, to provide the compound of the invention.

Other synthetic methods of possible utility are described in U.S. Ser. No. 11/899,758, filed Sep. 7, 2007, and U.S. Ser. No. 12/001,021, filed Dec. 7, 2007, both incorporated herein by reference in full.

The products can then be purified, e.g., by extraction, crystallization, preparative HPLC, flash chromatography, thin layer chromatography and the like.

Utility

The compounds of this invention are JNK modulators and as such are expected to be effective in the treatment of a wide range of JNK mediated disorders. Exemplary JNK mediated disorders include, but are not limited to, autoimmune disorder, inflammatory disorder, metabolic disorder, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

Additional objects, advantages, and novel features of this invention will become apparent to those skilled in the art upon examination of the following examples thereof, which are not intended to be limiting.

Additional objects, advantages, and novel features of this invention will become apparent to those skilled in the art upon examination of the following examples thereof, which are not intended to be limiting.

LIST OF ABBREVIATIONS

AcOH (Acetic acid); Bn (Benzyl); BOP (Benzotriazol-1-yloxytris(dimethylamino)phosphonium hexafluorophosphate); (BOC)$_2$O (Di-tert-butyl dicarbonate); CSI (Chlorosulfonyl isocyanate); DBU (1,8-Diazabicyclo[5.4.0]-undec-7-ene); DCM (Dichloromethane (methylene chloride)); DEA (Diethylamine); DIPEA (Diisopropylethylamine); DMF (N,N-dimethylformamide); EDCI (1-(3-Dimethylaminopropyl)-3-ethylcarbodiimide hydrochloride); Et$_2$O (Diethyl ether); EtOH (Ethanol); EtOAc (Ethyl acetate); HOBt (1-Hydroxybenzotriazole); i-PrOH (Isopropanol); LAH (Lithium aluminum hydride); m-CPBA ((also MCPBA) 3-Chloroperoxybenzoic acid); MeCN (Acetonitrile); MeOH (Methanol); MW (Microwaves); NCS (N-Chlorosuccinimide); NMP (1-Methyl-2-pyrrolidinone); p-TSA (p-Toluenesulfonic acid); RT (Room temperature); TEA (Triethylamine); THF (Tetrahydrofuran); TLC (Thin layer chromatography).

Example 1

Synthesis of 2-{3-[2-(4-methanesulfonylmethyl-cyclohexylamino)-pyrimidin-4-yl]-imidazo[1,2-a]pyridin-8-yl}-propan-2-ol (Compound 1)

(A) EtOH (500 mL) was added to 2-amino-nicotinic acid (25 g), followed by H$_2$SO$_4$ (25 mL, conc), and the mixture stirred at 75° C. overnight. The reaction mixture was then redissolved in H$_2$O, neutralized with Na$_2$CO$_3$ (aq), and the resulting precipitate filtered and dried to provide 2-amino-nicotinic acid ethyl ester, which was used without further purification.

(B) A mixture of 2-amino-nicotinic acid ethyl ester (13.845 g), ClCH$_2$CHO (58 mL), and NaHCO$_3$ (11.85 g) was stirred in EtOH (500 mL) at reflux overnight. The reaction mixture was concentrated, diluted with H2O, and extracted with DCM. The product was purified by ISCO using 100% EtOAc first (to remove unreacted starting material), then using 100% DCM to 5% MeOH/DCM. The product eluted at 3% MeOH/DCM, providing imidazo[1,2-a]pyridine-8-carboxylic acid ethyl ester (10.5 g).

(C) A mixture of imidazo[1,2-a]pyridine-8-carboxylic acid ethyl ester (3.5 g) in THF (200 mL) was treated with MeMgBr (4 equivalents, 3 M in Et$_2$O) dropwise at RT, and stirred overnight. The reaction mixture was quenched with water, extracted with EtOAc, and purified by ISCO using 100% EtOAc to provide 2-(imidazo[1,2-a]pyridin-8-yl)-propan-2-ol.

(D) To 2-(imidazo[1,2-a]pyridin-8-yl)-propan-2-ol (1.5 g) in DCM (250 mL) was added NBS (1.67 g), and the mixture stirred at RT for 1 h. The reaction mixture was then diluted with water, the organic layer extracted and dried over Na$_2$SO$_4$, filtered and concentrated.

The product was purified by ISCO using 20% EtOAc/hexane to 100% EtOAc to provide 2-(3-bromo-imidazo[1,2-a]pyridin-8-yl)-propan-2-ol (1.75 g).

(E) A solution of 2-(3-bromo-imidazo[1,2-a]pyridin-8-yl)-propan-2-ol (1.75 g) in dioxane was degassed in a 150 mL bottle, and purged with argon. To this was added 2-methylsulfanyl-4-tributylstannanyl-pyrimidine (2.85 g), Pd$_2$(dba)$_3$ (0.63 g) and Pt—Bu$_3$-HBF$_4$ (0.8 g) and CsF (2.1 g), the bottle sealed, and the mixture stirred at 100° C. overnight. The reaction mixture was then cooled to RT, filtered, and the filtrate concentrated and purified by ISCO using EtOAc/hexane to provide 2-[3-(2-methylsulfanyl-pyrimidin-4-yl)-imidazo[1,2-a]pyridin-8-yl]-propan-2-ol (0.675 g).

(F) A solution of 2-[3-(2-methylsulfanyl-pyrimidin-4-yl)-imidazo[1,2-a]pyridin-8-yl]-propan-2-ol (0.5 g) in DCM (100 mL) was cooled to 0° C., and MCPBA (0.376 g) was added. The reaction mixture was stirred at 0° C. for 2 h, then quenched with 10% Na$_2$S$_2$O$_3$ (aq). The organic layer was washed with NaHCO$_3$ (sat'd aq), separated, and dried over Na$_2$SO$_4$, filtered, concentrated, and titurated with EtOAc and filtered to provide 2-[3-(2-methylsulfinyl-pyrimidin-4-yl)-imidazo[1,2-a]pyridin-8-yl]-propan-2-ol (0.4 g).

(G) A mixture of 2-[3-(2-methylsulfinyl-pyrimidin-4-yl)-imidazo[1,2-a]pyridin-8-yl]-propan-2-ol (75 mg), 4-methanesulfonylmethyl-cyclohexylamine (162 mg), and TEA (0.165 mL) in NMP (2 mL) was stirred at 100° C. overnight. The reaction mixture was then cooled to RT, and diluted with water. The resulting precipitate was filtered and dried, then purified by ISCO using 100% DCM to 10% MeOH/DCM. The fractions were collected, concentrated, and titurated with EtOAc. The resulting solid was filtered and dried at 50° C. under vacuum overnight to provide 2-{3-[2-(4-methanesulfonylmethyl-cyclohexylamino)-pyrimidin-4-yl]-imidazo[1,2-a]pyridin-8-yl}-propan-2-ol (Compound 1, 55.5 mg). Mp=223-224° C.

Example 2

Synthesis of (4-{4-[8-(1-hydroxy-1-methyl-ethyl)-imidazo[1,2-a]pyridin-3-yl]-pyrimidin-2-ylamino}-cyclohexyl)-(4-hydroxy-piperidin-1-yl)-methanone (Compound 2)

(A) A mixture of 2-[3-(2-methylsulfinyl-pyrimidin-4-yl)-imidazo[1,2-a]pyridin-8-yl]-propan-2-ol (0.19 g), 4-amino-cyclohexanecarboxylic acid ethyl ester (0.31 g) in NMP (2 mL) was stirred at 100° C. for 3 h. The reaction mixture was cooled to RT, and diluted with water. The resulting solid was filtered and dried, then purified by ISCO using 100% DCM to 10% MeOH/DCM. Fractions were collected, concentrated, and titurated with EtOAc/hexane. The resulting solid was filtered and dried at 50° C. under vacuum overnight to provide 4-{4-[8-(1-hydroxy-1-methyl-ethyl)-imidazo[1,2-a]pyridin-3-yl]-pyrimidin-2-ylamino}-cyclohexanecarboxylic acid ethyl ester (0.215 g).

(B) A mixture of 4-{4-[8-(1-hydroxy-1-methyl-ethyl)-imidazo[1,2-a]pyridin-3-yl]-pyrimidin-2-ylamino}-cyclohexanecarboxylic acid ethyl ester (0.215 g), LiOH—H$_2$O (0.106 g), THF (20 mL), EtOH (5 mL) and water (5 mL) was stirred at RT overnight. The reaction mixture was then concentrated to remove THF and EtOH, neutralized with HCl (1 N), and the resulting solid filtered and dried at 50° C. under vacuum overnight to provide 4-{4-[8-(1-hydroxy-1-methyl-ethyl)-imidazo[1,2-a]pyridin-3-yl]-pyrimidin-2-ylamino}-cyclohexanecarboxylic acid (0.175 g), which was used without further purification.

(C) A mixture of 4-{4-[8-(1-hydroxy-1-methyl-ethyl)-imidazo[1,2-a]pyridin-3-yl]-pyrimidin-2-ylamino}-cyclohexanecarboxylic acid (0.175 g), BOP (0.39 g), DIEA (0.23 mL), and piperidin-4-ol (67 mg) in DMF (5 mL) was stirred at RT overnight. The resulting solid was filtered and dried, purified by ISCO using 100% DCM to 20% MeOH/DCM. The fractions were collected and concentrated, then titurated with EtOAc, and the resulting solid filtered and dried at 50° C. overnight to provide (4-{4-[8-(1-hydroxy-1-methyl-ethyl)-imidazo[1,2-a]pyridin-3-yl]-pyrimidin-2-ylamino}-cyclohexyl)-(4-hydroxy-piperidin-1-yl)-methanone (Compound 2, 140.4 mg). Mp=188.0-190.0° C.

Example 3

Synthesis of N-(4-{4-[8-(1-Hydroxy-1-methyl-ethyl)-imidazo[1,2-a]pyridine-3-yl]-pyrimidin-2-ylamino}-cyclohexyl)-methanesulfonamide (Compound 3)

A mixture of 2-[3-(2-methanesulfinyl-pyrimidin-4-yl)-imidazo[1,2-a]pyridine-8-yl]-propan-2-ol (0.15 g) and N-(4-amino-cyclohexyl)-methanesulfonamide (0.325 g) in NMP (1.5 mL) was treated with TEA (0.33 mL) and heated at 105° C. for 18 h. The reaction mixture was then cooled to RT and diluted with water. The resulting precipitate was filtered, washed with water, and dried. The product was purified by ISCO using 100% DCM to 15% MeOH/DCM. Pure fractions were collected, concentrated, and titurated with EtOAc. The resulting solid was filtered and dried at 50° C. under vacuum overnight to provide N-(4-{4-[8-(1-hydroxy-1-methyl-ethyl)-imidazo[1,2-a]pyridine-3-yl]-pyrimidin-2-ylamino}-cyclohexyl)-methanesulfonamide (compound 3, 84.9 mg).

Example 4

Synthesis of N-(4-{4-[8-(1-Hydroxy-1-methyl-ethyl)-imidazo[1,2-a]pyridine-3-yl]-pyrimidin-2-ylamino}-cyclohexyl)-(N,N-dimethylamino)sulfonamide (Compound 4)

A mixture of 2-[3-(2-methanesulfinyl-pyrimidin-4-yl)-imidazo[1,2-a]pyridine-8-yl]-propan-2-ol (0.14 g) and N-(4-amino-cyclohexyl)-N',N'-dimethylaminosulfonamide (0.34 g) in NMP (2 mL) was treated with TEA (0.31 mL) and heated at 100° C. for 8 h. The reaction mixture was then cooled to RT and diluted with water. The product was extracted with EtOAc and purified by ISCO using 100% DCM to 15% MeOH/DCM to provide N-(4-{4-[8-(1-hydroxy-1-methyl-ethyl)-imidazo[1,2-a]pyridine-3-yl]-pyrimidin-2-ylamino}-cyclohexyl)-(N',N'-dimethyl)sulfonamide (compound 4, 70 mg).

Example 5

Synthesis of (4-Hydroxy-piperidin-1-yl)-(4-{4-[8-(3-methanesulfonyl-propoxy)-imidazo[1,2-a]pyridin-3-yl]-pyrimidin-2-ylamino}-cyclohexyl)-methanone (Compound 5)

(A) A mixture of 3-benzyloxy-2-aminopyridine (25.0 g), chloroacetaldehyde (16.7 mL, 50% aq solution), and EtOH (200 mL) were heated in a sealed 500 mL tube at 80° C. for 19 h. The reaction mixture was then cooled to RT and concentrated to a residue. The residual oil was taken up in NaOH (1 N aq, 125 mL) and extracted with DCM. The organic layer was washed with water, dried over Na2SO4, and concentrated to provide a solid, which was dried overnight under vacuum. The product, 8-benzyloxy-imidazo[1,2-a]pyridine (25.6 g) was used without further purification.

(B) To a solution of 8-benzyloxy-imidazo[1,2-a]pyridine (25.46 g) in EtOH (250 mL) was added Br$_2$ (7.03 mL) in water (7 mL) dropwise at RT. The resulting dark orange suspension was stirred at RT for 1 h. The reaction mixture was diluted with NaOH (90 mL, 1 N) and extracted with DCM. The organic layer was dried over Na$_2$SO$_4$, filtered, and concentrated. The product crashed in the column and tubing during attempted purification. Recovered product provided 8-benzyloxy-3-bromo-imidazo[1,2-a]pyridine (21 g).

(C) A solution of 8-benzyloxy-3-bromo-imidazo[1,2-a]pyridine (18.7 g) in dioxane (150 mL) was added to a 350 mL tube and degassed. To this was added Pd$_2$(dba)$_3$ (1.122 g), P(cyc)$_3$ (1.37 g), 4,4,5,5,4',4',5',5'-octamethyl-[2,2']bi[1,3,2]dioxaborolanyl] (18.7 g), and KOAc (18.14 g), and the mixture stirred at 95° C. overnight. The reaction mixture was cooled to RT, and diluted with water and EtOAc. The organic layer was separated, dried over Na$_2$SO$_4$, filtered, and concentrated. The residue was titurated with EtOAc, and the resulting solid filtered and dried. The product was taken up in hot EtOAc, heated with a heat gun, and filtered hot. The filtrate was cooled, and the solid separated, filtered, and dried under vacuum at 50° C. overnight to provide 8-benzyloxy-3-(4,4,5,5-tetramethyl[1,3,2]dioxaborolan-2-yl)-imidazo[1,2-a]pyridine (1.67 g).

(D) Into a 350 mL tube was placed 2,4-dichloropyrimidine (1.95 g) in MeCN (100 mL), and the mixture degassed. To this was added palladium tetra(triphenylphosphine) (Pd(PPh$_3$)$_4$, 0.5 g), followed by Na$_2$CO$_3$ (1.85 g in 100 mL water) and 8-benzyloxy-3-(4,4,5,5-tetramethyl[1,3,2]dioxaborolan-2-yl)-imidazo[1,2-a]pyridine (1.167 g). The reaction mixture was degassed, the tube purged with argon and sealed, and the mixture stirred at 95° C. overnight. The reaction mixture was then cooled to RT and concentrated, extracted with EtOAc, and purified by ISCO using 50% EtOAc/hexane to 100% EtOAc. Pure fractions were collected and concentrated, and the residue titurated with EtOAc. The resulting solid was filtered and dried at 50° C. under vacuum overnight to provide 8-benzyloxy-3-(2-chloropyrimidin-4-yl)-imidazo[1,2-a]pyridine (0.5 g).

(E) A mixture of 8-benzyloxy-3-(2-chloropyrimidin-4-yl)-imidazo[1,2-a]pyridine (0.19 g) and 4-amino-cyclohexanecarboxylic acid ethyl ester (0.29 g) in NMP (1 mL) was stirred at 100° C. for 1 h. The reaction mixture was cooled to RT, diluted with water, and the resulting solid separated, washed with water, and dried. The solid was titurated with hot EtOAc and filtered to provide 4-[4-(8-benzyloxy-imidazo[1,2-a]pyridine-3-yl)-pyrimidin-2-ylamino]-cyclohexanecarboxylic acid ethyl ester (compound 8, 0.25 g), which was used without further purification.

(F) A mixture of 4-[4-(8-benzyloxy-imidazo[1,2-a]pyridine-3-yl)-pyrimidin-2-ylamino]-cyclohexanecarboxylic acid ethyl ester (0.215 g) and Pd/C (10%, 600 mg) in EtOH (200 mL) was stirred under H$_2$ overnight. The reaction mixture was heated and filtered hot through silica. The product was washed with DCM, and the filtrate concentrated and dried to provide 4-[4-(8-hydroxy-imidazo[1,2-a]pyridine-3-yl)-pyrimidin-2-ylamino]-cyclohexanecarboxylic acid ethyl ester (128 mg), which was used without further purification.

A mixture of 4-[4-(8-hydroxy-imidazo[1,2-a]pyridine-3-yl)-pyrimidin-2-ylamino]-cyclohexanecarboxylic acid ethyl ester (0.127 g), 1-chloro-3-methanesulfonyl-propane (63.5 mg), K$_2$CO$_3$ (137 mg), and NaI (5 mg) in NMP (1 mL) was stirred at 90° C. for 1 h. The reaction mixture was cooled to RT and diluted with water. The resulting solid was filtered and washed with water, then dried and purified by ISCO using 100% DCM to 20% MeOH/DCM to provide 4-{4-[8-(3-methanesulfonyl-propoxy)-imidazo[1,2-a]pyridine-3-yl]-pyrimidin-2-ylmethyl}-cyclohexanecarboxylic acid ethyl ester (0.1 g).

(H) A mixture of 4-{4-[8-(3-methanesulfonyl-propoxy)-imidazo[1,2-a]pyridine-3-yl]-pyrimidin-2-ylamino}-cyclohexanecarboxylic acid ethyl ester (0.1 g) and LiOH—H$_2$O (42 mg) in THF (20 mL), EtOH (5 mL) and water (5 mL) was stirred at RT overnight. The reaction mixture was then concentrated, diluted with water, neutralized with HCl (1 N), and the resulting solid filtered and dried at 50° C. under vacuum overnight to provide 4-{4-[8-(3-methanesulfonyl-propoxy)-imidazo[1,2-a]pyridine-3-yl]-pyrimidin-2-ylamino}-cyclohexanecarboxylic acid (90 mg), which was used without further purification.

(I) A solution of 4-{4-[8-(3-methanesulfonyl-propoxy)-imidazo[1,2-a]pyridine-3-yl]-pyrimidin-2-ylamino}-cyclohexanecarboxylic acid (0.09 g) in DMF (3 mL) was treated with BOP (0.126 g), and the mixture stirred at RT for 15 min DIEA (0.1 mL) and piperidin-4-ol (29 mg) were added, and the mixture stirred at RT overnight. The reaction mixture was then diluted with water and stirred at RT for 30 min, permitting the product to precipitate. The resulting solid was filtered, washed with water, dried, and titurated with EtOAc. The product was filtered, dried at 50° C. under vacuum overnight to provide (4-hydroxy-piperidin-1-yl)-(4-{4-[8-(3-methanesulfonyl-propoxy)-imidazo[1,2-a]pyridin-3-yl]-pyrimidin-2-ylamino}-cyclohexyl)-methanone (compound 5, 71 mg).

Example 6

Synthesis of {4-[4-(8-Benzyloxy-imidazo[1,2-a]pyridin-3-yl)-pyrimidin-2-ylamino]-cyclohexyl}-(4-hydroxy-piperidin-1-yl)-methanone (Compound 6)

A mixture of 4-[4-(8-benzyloxy-imidazo[1,2-a]pyridine-3-yl)-pyrimidin-2-ylamino]-cyclohexanecarboxylic acid ethyl ester (0.23 g) in DMF (10 mL) was treated with BOP (79 mg), then DIEA (0.345 g), then piperidin-4-ol (79 mg), and the mixture stirred at RT for 5 h. The reaction mixture was then diluted with water, and the resulting solid filtered, washed with water, and dried. The solid was then dissolved in hot EtOAc, MeOH, and DCM, and the solution filtered hot. The product was dried at 50° C. under vacuum overnight to provide {4-[4-(8-benzyloxy-imidazo[1,2-a]pyridin-3-yl)-pyrimidin-2-ylamino]-cyclohexyl}-(4-hydroxy-piperidin-1-yl)-methanone (compound 6, 244 mg).

Example 7

Synthesis of N-{4-[4-(8-benzyloxy-imidazo[1,2-a]pyridin-3-yl)-pyrimidin-2-ylamino]-cyclohexyl}-methanesulfonamide (Compound 7)

A mixture of 8-benzyloxy-3-(2-chloropyrimidin-4-yl)-imidazo[1,2-a]pyridine (0.1 g), N-(4-amino-cyclohexyl)-methanesulfonamide (0.2 g), and TEA (0.21 mL) in NMP (2 mL) was stirred at 100° C. overnight. The reaction mixture was cooled to RT, diluted with water, and the resulting solid filtered, washed with water, and dried. The product was purified by ISCO 2x using 100% DCM to 15% MeOH/DCM. Pure fractions were collected, concentrated, and titurated with EtOAc. The resulting solid was filtered and dried at 50° C. under vacuum overnight to provide N-{4-[4-(8-benzyloxy-imidazo[1,2-a]pyridin-3-yl)-pyrimidin-2-ylamino]-cyclohexyl}-methanesulfonamide (compound 7, 14 mg).

Example 8

Synthesis of 4-[4-(8-Benzyloxy-imidazo[1,2-a]pyridin-3-yl)-pyrimidin-2-yl-amino]-cyclohexanol (Compound 9)

A mixture of 8-benzyloxy-3-(2-chloro-pyrimidin-4-yl)-imidazo[1,2-a]pyridine (0.1 g) and 4-amino-cyclohexanol (0.1 g) in NMP (2 mL) was stirred at 100° C. for 3 h. The reaction mixture was then cooled to RT, diluted with water, and the resulting solid filtered, washed with water, and dried. The product was purified by ISCO using 100% DCM to 15% MeOH/DCM. Pure fractions were collected and concentrated. The residue was titurated with EtOAc, and the solid filtered and dried at 50° C. under vacuum overnight to provide N-[1-(8-benzyloxy-imidazo[1,2-a]pyridin-3-yl)-pyrimidin-2-ylamino]-cyclohexanol (compound 9, 84.8 mg).

Example 9

Synthesis of N-[4-(4-Imidazo[1,2-a]pyridin-3-yl-pyrimidin-2-ylamino)-cyclohexyl]-methanesulfonamide (Compound 10)

(A) A solution of 2,4-dichloropyimidine (0.9 g) in MeCN (25 mL) was degassed, then treated with Pd(PPh$_3$)$_4$ (0.348 g), 3-(4,4,5,5-tetramethyl-[1,3,2]dioxaborolan-2-yl)-imidazo[1,2-a]pyridine (0.75 g), and Na$_2$CO$_3$ (0.954 g in 25 mL water). The reaction mixture was degassed and stirred at 100° C. overnight. The reaction mixture was then cooled to RT and diluted with water, and the resulting solid filtered, washed with water, and dried. The product was purified by ISCO using 100% DCM to 10% MeOH/DCM, the fractions combined and concentrated, and the residue titurated with EtOAc. The resulting solid was filtered, washed with EtOAc, and dried under vacuum overnight to provide 3-(2-chloropyrimidin-4-yl)-imidazo[1,2-a]pyridine (125 mg).

(B) A mixture of 3-(2-chloropyrimidin-4-yl)-imidazo[1,2-a]pyridine (0.125 g), N-(4-amino-cyclohexyl)-methanesulfonamide (0.372 g), and TEA (0.38 mL) in NMP (3 mL) was stirred at 105° C. for 10 h. The reaction mixture was cooled to RT, diluted with water, and the resulting solid filtered, washed with water, and dried. The product was purified by ISCO using 100% DCM to 15% MeOH/DCM, the pure fractions combined and concentrated, then titurated with EtOAc. The resulting solid was filtered and dried at 50° C. under vacuum overnight to provide N-[4-(4-imidazo[1,2-a]pyridin-3-yl-pyrimidin-2-ylamino)-cyclohexyl]-methanesulfonamide (compound 10, 5.8 mg).

Example 10

Synthesis of 4-(4-Imidazo[1,2-a]pyridin-3-yl-pyrimidin-2-ylamino)-cyclohexanol (Compound 11)

A mixture of 3-(2-chloropyrimidin-4-yl)-imidazo[1,2-a]pyridine (30 mg) and 4-amino-cyclohexanol (45 mg) in NMP (1 mL) was stirred at 105° C. for 5 h. The reaction mixture was then cooled to RT and titurated with water. The resulting solid was filtered, washed with water and dried. The product was purified by ISCO using 100% DCM to 15% MeOH/DCM, and the pure fractions combined, concentrated, and titurated with EtOAc. The resulting solid was filtered and dried at 50° C. under vacuum overnight to provide 4-(4-imidazo[1,2-a]pyridin-3-yl-pyrimidin-2-ylamino)-cyclohexanol (compound 11, 22 mg).

Example 11

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K ® (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2-2 |
| SPAN ® 60 | 2 |
| TWEEN ® 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethyl-cellulose, dextrose, and the like. Hydrochloric acid may be added to adjust pH. The nasal spray formulations may be delivered via a nasal spray metered pump typically delivering about 50-100 μL of formulation per actuation. A typical dosing schedule is 2-4 sprays every 4-12 h.

Example 12

JNK Assay In Vitro

JNK activity was measured by phosphorylation of GST-ATF2 (19-96) with [γ-$^{33}$P] ATP. The enzyme reaction was conducted at Km concentrations of ATP and the substrate at final volume of 40 μl in buffer containing 25 mM HEPES, pH 7.5, 2 mM dithiothreitol, 150 mM NaCl, 20 mM MgCl$_2$, 0.001% Tween® 20, 0.1% BSA and 10% DMSO. Human JNK2α2 assay contains 1 nM enzyme, 1 μM ATF2, 8 μM ATP with 1 μCi [γ-$^{33}$P] ATP. Human JNK1α1 assay contains 2 nM enzyme, 1 μM ATF2, 6 μM ATP with 1 μCi [γ-$^{33}$P] ATP. Human JNK3 (Upstate Biotech #14-501M) assay contains 2 nM enzyme, 1 μM ATF2, 4 μM ATP with 1 μCi [γ-$^{33}$P] ATP. The enzyme assay was carried out in the presence or absence of several compound concentrations. JNK and compound were pre-incubated for 10 min, followed by initiation of the enzymatic reaction by adding ATP and the substrate. The reaction mixture was incubated at 30° C. for 30 min. At the end of incubation, the reaction was terminated by transferring 25 μl of the reaction mixture to 150 μl of 10% glutathione Sepharose® slurry (Amersham #27-4574-01) containing 135 mM EDTA. The reaction product was captured on the affinity resin, and washed on a filtration plate (Millipore, MAB-VNOB50) with phosphate buffered saline for six times to remove free radionucleotide. The incorporation of $^{33}$P into ATF2 was quantified on a microplate scintillation counter (Packard Topcount). Compound inhibition potency on JNK was measured by IC$_{50}$ value generated from ten concentration inhibition curves fitted into the 3-parameter model: % inhibition=Maximum/(1+(IC$_{50}$/[Inhibitor])$^{slope}$). Data were analyzed on Microsoft Excel for parameter estimation. The results are shown in Table 2 below:

TABLE 2

Inhibition of Human JNK

| Compound | JNK1 – IC$_{50}$ (μM) | JNK2 – IC$_{50}$ (μM) |
|---|---|---|
| 1 | | 0.2949 |
| 2 | | 0.3691 |
| 3 | | 0.1233 |
| 4 | | 0.1238 |
| 5 | 0.0216 | 0.0503 |
| 6 | 0.0333 | 0.0559 |
| 7 | 0.0237 | 0.0527 |
| 8 | 0.0489 | 0.1043 |
| 9 | 0.0269 | 0.0494 |
| 10 | 0.0567 | 0.2138 |
| 11 | 0.0866 | 0.2535 |

Example 13

Phospho-c-Jun Translocation Assay

Inflammation is regulated in part by the action of c-Jun on other genes in the inflammatory pathway. Thus, inhibition of phosphorylated c-Jun translocation to the nucleus provides an indication of the anti-inflammatory activity of a compound. SW1353 cells are purchased from the American Tissue Culture Collection and maintained in growth media containing DMEM medium (Invitrogen) with 10% fetal bovine serum (Invitrogen), ascorbic acid (Sigma), and penicillin/streptomycin/glutamate (Invitrogen) under culture conditions (at 37° C. with 5% CO$_2$). Cells are plated at a density of 8,000 cells/well in 100 μl growth medium 24 h prior to the compound treatment. Immediately before the compound treatment, growth media is replaced with 90 μl of fresh media. Compound stock at 10 mM is first diluted in compound vehicle (DMSO) to 3 mM, then diluted in serum-free medium and added to each well as a 10× concentrated solution in a volume of 10 μl, mixed, and pre-incubated with cells for 30 min at 37° C. in 5% CO$_2$. Compound vehicle (DMSO) is maintained at a final concentration of 1% for all samples. After 30 min incubation, the cells are activated with TNFα (1 ng/ml, Roche Biochem) for 20 min Cells are then fixed, permeabilized, and stained with anti-phospho-c-Jun antibody (Santa Cruz), followed by Alexa Fluor 488 labeled secondary antibody and Hoechet 33342 dye (Invitrogen) per manufacturer's instructions. The signals of phospho-c-Jun are measured for 400 cells per well by the ArrayScan HCS system (Cellomic). The IC$_{50}$ values are calculated as the concentration of the compound at which the phospho-c-Jun activity was inhibited to 50% of the control value using the 4-parameter fitting function in the ActivityBase program (IDBS).

Example 14

Rat In Vivo TNFα-Induced IL-6 Production Assay

Female Wistar-Han rats procured from Charles River Laboratories are allowed to acclimate for one week prior to use and to achieve an approximate body weight of 95-130 g. Rats are administered test compound via oral gavage 30 min prior to an intraperitoneal challenge of 0.5 μg recombinant rat TNF-α (Biosource). Blood is collected via cardiocentesis 90 min after TNF-α challenge. Plasma is prepared using lithium heparin separation tubes (BD microtainer) and frozen at −80° C. until analyzed. IL-6 levels are determined using a rat specific IL-6 ELISA kit (Biosource). The percent inhibition and ED$_{50}$ values (calculated as the dose of compound at which TNF-α production is 50% of the control value) are determined. The results demonstrate that compounds of the invention inhibit TNFα-induced IL-6 production.

Example 15

Rodent Collagen-Induced Arthritis

Female Lewis rats procured from Harlan Laboratories at 7-8 weeks of age are allowed to acclimate for one week prior to use and achieve an approximate body weight of 120-140 g. On day 0 of study, rats are primed intradermally (i.d.) on several sites on the back with an emulsion of 100 μg Bovine Type II Collagen (Chondrex) in Incomplete Freund's adjuvant (IFA; total of 0.1 ml in 2-3 sites). Arthritis induction is generally observed 12-14 days from priming; however a booster injection of 100 μg collagen/IFA is given around days 7-10 (i.d. up to 0.1 ml total) at the base of the tail or an alternate site on back to synchronize disease induction. Compound dosing can be prophylactic (starting at time of boost or 1-2 days prior) or therapeutic (beginning after boost and coinciding with initial disease scores of 1-2—see clinical scoring below). Animals are evaluated for the development and progression of disease over the next 21 days.

Rats are evaluated using a scoring system (described below), paw volume measurements using a plethysmometer for each paw, or measuring paw or joint thickness with a caliper. Baseline measurements are performed on day 0, and starting again at the first signs of swelling for up to three times per week until the end of the experiment. Scoring is evaluated as follows for each paw:
1=swelling and/or redness of paw or one digit.
2=swelling in two or more joints.
3=gross swelling of the paw with more than two joints involved.
4=severe arthritis of the entire paw and digits.

The arthritic index for each rat is evaluated by adding the four scores of the individual paws, giving a maximum score of 16. In order to serially measure disease onset and progression, the paw volume of the hind paws is also determined through the use of a plethysmometer.

At the end of the study, the hind paws (and other tissues) are harvested for weight determination, histology, cellular and/or molecular analysis. Additionally, blood is collected via cardiocentesis, plasma is prepared using lithium heparin separation tubes (BD microtainer) and frozen at −70° C. until analyzed. Inflammatory cytokine levels (e.g., TNF-α, IL-1 and IL-6) from the plasma or from homogenized joint tissue are determined using rat-specific ELISA kits (R&D). The level of disease protection or inhibition is determined as a composite of changes in clinical scores, paw volumes and histopathology compared to control animals.

Example 16

IL-8 Production Assay in TNFα-Induced Human Chondrosarcoma SW1353 Cells

SW1353 cells are purchased from the American Tissue Culture Collection and maintained in growth media consisting of DMEM medium (Invitrogen) with 10% fetal bovine serum (Invitrogen), ascorbic acids (Sigma) and penicillin (Invitrogen) under the culture condition of 37° C. in 5% $CO_2$. Cells are plated at a density of $1.0 \times 10^4$ cells per well in 100 μl of media 48 hours before the compound treatment. Immediately before the compound treatment, media is replaced with 160 μl of fresh media. Compound stock (10 mM) is diluted in growth media and added to each well as a 10× concentrated solution in a volume of 20 μl, mixed and allowed to pre-incubate with cells for 30 min. The compound vehicle (DMSO) is maintained at a final concentration of 1% in all samples. After 30 min, the cells are activated with 10 ng/ml of TNF-α (Roche Biochem). TNF-α is added as a 10× concentrated solution made up in growth media and added in a volume of 20 μl per well. Cell plates are cultured for 5 h. Cell media are harvested and stored at −20° C. Media aliquots are analyzed by sandwich ELISA for the presence of IL-8 as per the manufacturer's instructions (BD Bioscience). The $IC_{50}$ values are calculated as the concentration of the compound at which the IL-8 production was reduced to 50% of the control value using Xlfit3 in Microsoft Excel program. Certain compounds have an $IC_{50}$ value ranging from 0.1-20 μM in this assay.

Example 17

Ovalbumin-Sensitized Asthma Model (A) Male Brown-Norway rats are sensitized i.p. with 100 μg of OA (ovalbumin) in 0.2 ml alum once every week for three weeks (day 0, 7, and 14). The week following the last sensitization, the rats are ready for testing. One to 2 days prior to challenge, animals are weighed. On day 21, the rats are dosed q.d. with either vehicle or compound formulation subcutaneously 30 minutes before OA aerosol challenge (1% OA for 45 minutes) and terminated 4 or 24 hours after challenge. At time of sacrifice, rats are anesthetized (urethane, approx. 2 g/kg, i.p.). Plasma is collected from rats for PK at termination. Blood is drawn from the abdominal aorta at termination. A tracheal cannula is inserted and the lungs are lavaged with 3×3 ml PBS. The BAL fluid is analyzed for total leukocyte number and differential leukocyte counts. Total leukocyte number in an aliquot of the cells (20-100 μl) is determined using a Coulter Counter. For differential leukocyte counts, 50-200 μl of the sample is centrifuged in a Cytospin and the slide stained with Diff-Quik. The proportions of monocytes, eosinophils, neutrophils and lymphocytes are counted under light microscopy using standard morphological criteria and expressed as a percentage. The remaining BAL fluid is centrifuged (1500 rpm, 10 min) and the supernatant is stored at −80° C. Lungs are also harvested for protein and/or RNA analyses.

Example 18

CFA Induced Thermal Hyperalgesia Assay

Male Wistar rats (~200 g) are purchased from Charles River Laboratories. Food and water are allowed ad-libitum prior to study. On Day 0 animals are injected with 50 μl (1.0 mg/ml) of 100% Complete Freund's Adjuvant (CFA; Sigma Chemical Co, St. Louis, Mo., USA) into the plantar side of the right hind paw under isoflurane anesthesia. Following recovery from anesthesia, rats are moved to the study room and placed in the clear rectangle plastic boxes where the thermal hyperalgesia test is to be performed for 30 min. After habituation, rats are returned to their normal housing.

On Day 1, rats are fasted overnight, and on Day 2 (48 h post CFA injection) rats are moved back to the study room and habituated to the room for at least 1 h. Rats are then placed individually in clear plastic boxes atop a clear plastic floor for 10 min before the study begins. The Hargreaves test is used to measure thermal paw withdrawal thresholds. Fiber optic radiant heat (intensity setting 60) using a plantar tester (Ugo Basile, Italy) is applied through the plastic floor to each rear hind paw. The time for the rat to remove its paw from the heat source is recorded. The target threshold for the contra-lateral paw was ~10 s. Each paw is tested 3× with at least a 5 min interval, alternating between the ipsi-lateral and contra-lateral paws. After the baseline is determined, rats are dosed with either vehicle or drug and the test repeated as above 30-120 min post dose. The tester is blinded to the treatment groups. Rats are euthanized by $CO_2$ inhalation at the end of the study, and observed for 5 to 10 min to ensure death occurs. Compounds of the invention effectively reduce pain in this assay.

What is claimed is:

1. A compound of formula I:

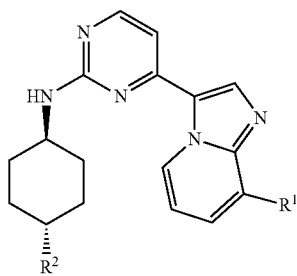

(I)

wherein
$R^1$ is —OH, —OR, or hydroxy-lower alkyl, where R is lower alkyl, benzyl, aryl-lower alkyl, or methylsulfonyl-lower alkyl;
$R^2$ is —OH, —$NH_2$, —$CH_2SO_2R^4$, —$SO_2R^4$—$NHSO_2R^4$, —$CO_2R^5$, or

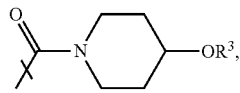

where $R^3$ is H, lower acyl, or an amino acid; $R^4$ is lower alkyl, —$NH_2$, lower alkyl-amino, or di(lower alkyl) amino; $R^5$ is H or lower alkyl;
or a pharmaceutically acceptable salt thereof.

2. The compound of claim 1, wherein
$R^1$ is —OH, —OR, or hydroxy-lower alkyl, where R is lower alkyl, benzyl, aryl-lower alkyl, or methylsulfonyl-lower alkyl;
$R^2$ is —OH, —$NH_2$, —$SO_2R^4$, —$NHSO_2R^4$, —$CO_2R^5$, or

where $R^3$ is H, lower acyl, or an amino acid; $R^4$ is lower alkyl, —$NH_2$, lower alkyl-amino, or di(lower alkyl)-amino; $R^5$ is H or lower alkyl;
or a pharmaceutically acceptable salt thereof.

3. The compound according to claim 2, wherein $R^2$ is —$NHSO_2CH_3$.

4. The compound according to claim 2, wherein $R^1$ is 2-hydroxy-prop-2-yl.

5. The compound according to claim 2, wherein $R^1$ benzyloxy.

6. The compound according to claim 2, wherein $R^2$ is 4-hydroxy-piperidin-1-carbonyl.

7. The compound of claim 6, wherein $R^1$ is 2-hydroxy-prop-2-yl.

8. The compound of claim 6, wherein $R^1$ is benzyloxy.

9. The compound of claim 6, wherein $R^1$ is 3-methanesulfonylpropoxy.

10. The compound of claim 1, wherein $R^2$ is —$NHSO_2N(CH_3)_2$.

11. The compound of claim 1, selected from the group consisting of:
2-{3-[2-(4-methanesulfonylmethyl-cyclohexylamino)-pyrimidin-4-yl]-imidazo[1,2-a]pyridine-8-yl}-propan-2-ol;
(4-{4-[8-(1-hydroxy-1-methyl-ethyl)-imidazo[1,2-a]pyridin-3-yl]-pyrimidin-2-ylamino}-cyclohexyl)-(4-hydroxy-piperidin-1-yl)-methanone;
N-(4-{4-[8-(1-hydroxy-1-methyl-ethyl)-imidazo[1,2-a]pyridine-3-yl]-pyrimidin-2-ylamino}-cyclohexyl)-methanesulfonamide;
N-(4-{4-[8-(1-hydroxy-1-methyl-ethyl)-imidazo[1,2-a]pyridine-3-yl]-pyrimidin-2-ylamino}-cyclohexyl)-(N,N-dimethylamino)sulfonamide;
(4-hydroxy-piperidin-1-yl)-(4-{4-[8-(3-methanesulfonylpropoxy)-imidazo[1,2-a]pyridin-3-yl]-pyridmidin-2-ylamino}-cyclohexyl)-methanone;
{4-[4-(8-benzyloxy-imidazo[1,2-a]pyridin-3-yl)-pyrimidin-2-ylamino]-cyclohexyl}-(4-hydroxy-piperidin-1-yl)-methanone;
N-{4-[4-(8-benzyloxy-imidazo[1,2-a]pyridin-3-yl)-pyrimidin-2-ylamino]-cyclohexyl}-methanesulfonamide;
4-[4-(8-benzyloxy-imidazo[1,2-a]pyridin-3-yl)-pyrimidin-2-ylamino]-cyclohexanecarboxylic acid ethyl ester; and
4-[4-(8-benzyloxy-imidazo[1,2-a]pyridin-3-yl)-pyrimidin-2-ylamino]-cyclohexanol.

12. A pharmaceutical composition for treating inflammation, comprising: an effective amount of a compound of Formula I:

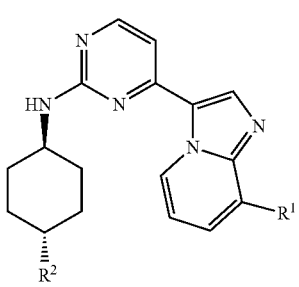

(I)

wherein
$R^1$ is —OH, —OR, or hydroxy-lower alkyl, where R is lower alkyl, benzyl, aryl-lower alkyl, or methylsulfonyl-lower alkyl;
$R^2$ is —OH, —$NH_2$, —$SO_2R^4$, —$NHSO_2R^4$, —$CO_2R^5$, or

where R³ is H, lower acyl, or an amino acid; R⁴ is lower alkyl, —NH₂, lower alkyl-amino, or di(lower alkyl)amino; R⁵ is H or lower alkyl;
or a pharmaceutically acceptable salt thereof;
and a pharmaceutically acceptable excipient.

13. A method of treating a subject for inflammation, said method comprising:
administering to a subject in need thereof an effective amount of a compound of formula I:

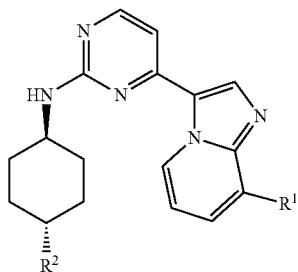

wherein
R¹ is —OH, —OR, or hydroxy-lower alkyl, where R is lower alkyl, benzyl, aryl-lower alkyl, or methylsulfonyl-lower alkyl;
R² is —OH, —NH₂, —SO₂R⁴, —NHSO₂R⁴, —CO₂R⁵, or

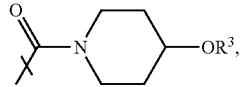

where R³ is H, lower acyl, or an amino acid; R⁴ is lower alkyl, —NH₂, lower alkyl-amino, or di(lower alkyl)-amino; R⁵ is H or lower alkyl;
or a pharmaceutically acceptable salt thereof.

14. A method of inhibiting the activity of JNK, comprising:
contacting said JNK with an effective concentration of a compound of formula I:

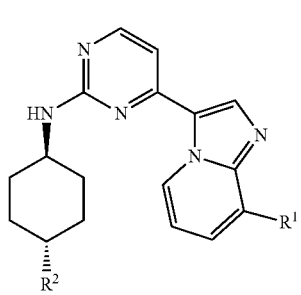

wherein
R¹ is —OH, —OR, or hydroxy-lower alkyl, where R is lower alkyl, benzyl, aryl-lower alkyl, or methylsulfonyl-lower alkyl;
R² is —OH, —NH₂, —SO₂R⁴, —NHSO₂R⁴, —CO₂R⁵, or

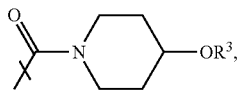

where R³ is H, lower acyl, or an amino acid; R⁴ is lower alkyl, —NH₂, lower alkyl-amino, or di(lower alkyl)-amino; R⁵ is H or lower alkyl;
or a pharmaceutically acceptable salt thereof.

* * * * *